United States Patent [19]
Dickinson et al.

[11] Patent Number: 5,274,721
[45] Date of Patent: Dec. 28, 1993

[54] FIBER OPTIC SYSTEM AND METHOD

[75] Inventors: William D. Dickinson, Medina, N.Y.; Richard Wissenbach, Chelmstad, Mass.; Donald Kaiser, Clarence Center; Dean Agostini, Middleport, both of N.Y.

[73] Assignee: American Sigma, Inc., Medina, N.Y.

[21] Appl. No.: 846,602

[22] Filed: Mar. 5, 1992

[51] Int. Cl.⁵ ............................. G02B 6/00; G02B 6/36
[52] U.S. Cl. ................................. 385/31; 250/227.14; 385/12
[58] Field of Search ................. 250/227.14; 385/12, 385/31, 32, 33

[56] References Cited

U.S. PATENT DOCUMENTS

| | | | |
|---|---|---|---|
| 4,270,049 | 5/1981 | Tanaka et al. | 385/12 X |
| 4,846,548 | 7/1989 | Klainer | 385/145 X |
| 4,893,894 | 1/1990 | Caimi | 385/12 |

*Primary Examiner*—Akm E. Ullah
*Attorney, Agent, or Firm*—Irving M. Weiner; Joseph P. Carrier; Pamela S. Burt

[57] ABSTRACT

A fiber optic system and method in which the transmission of light through a fiber optic core of a fiber optic element is stabilized and optimized by eliminating the destabilizing effect of light independently propagated along the clad of the fiber optic element. The propagation of light along the clad may be essentially eliminated by a field stop member disposed between a light-receiving end of the fiber optic element and an LED light source, whereby light from the LED is entirely shielded from the clad. The field stop member is particularly effective when used in a fiber optic sensor, wherein the effect of clad light on transmission of light through the core is particularly destabilizing. Alternative structures for mitigating or eliminating the destabilizing effect of clad light are also provided in the form of alterations of the clad structure, or by providing a clad light stop diaphragm at the light-emitting end of the fiber optic element. Also provided is an aperture stop member, which may or may not be integrally formed with the field stop member, to optimize light propagation along the core by focusing light from an LED onto the light-receiving end of the core.

22 Claims, 4 Drawing Sheets

FIBER OPTIC SYSTEM AND METHOD

BACKGROUND OF THE INVENTION

1. Field of the Invention

The invention relates generally to an improved fiber optic system in which the transmission of light along a fiber optic core of the system is stabilized and optimized. More particularly, the invention provides an apparatus and method which eliminates the destabilizing effect of light propagated in a clad surrounding the fiber optic core of a fiber optic element, by preventing light from being directly input from a photoemitter to the clad and/or by preventing light from being transmitted from the clad to a photodetector. The improved fiber optic system according to the invention further provides a means and apparatus for controlling the light input from the photoemitter to the fiber optic core by providing an aperture stop means between the photoemitter and the fiber optic element.

The terminology "fiber optic system" as used herein refers to a system of the type having a fiber optic element including a fiber optic core made of highly light-transmissive optical fiber for transmitting light from a photoemitter to a photodetector. The fiber optic element further includes a clad surrounding the fiber optic core, the clad being made of material having a lower refractive index than that of the core. Typically, the photoemitter takes the form of a light-emitting diode (LED). Light input to the fiber optic core by the LED traverses the core and becomes incident on the photodetector, which converts the modulated light into an electrical output signal which may be amplified for recording data.

The terminology "fiber optic sensor" as used herein refers to any one of a variety of types of fiber optic sensors, including one in which at least a portion of the clad of the fiber optic element is made of a material responsive to an analyte of interest. The clad material is responsive to a given chemical(s) or other analyte, such that its refractive index changes in the presence of such analyte(s) to thereby alter the light-transmitting properties of the sensor.

The term "analyte" as used herein refers to a chemical or physical property desired to be detected and/or measured in a medium of interest. By way of example, an analyte may refer to a given chemical or class of chemicals, a chemical compound or class of chemical compounds, water, biological agents, pressure, temperature, and the like.

2. Description of Relevant Art

There are generally known numerous types of fiber optic sensors for detecting and/or measuring an analyte of interest by employing the inherent light-transmission properties of an optical fiber. Illustrative of a known type of fiber optic sensor is the "Fiber Optic which is an Inherent Chemical Sensor" disclosed in U.S. Pat. No. 4,846,548 issued in 1989 to Klainer.

Figure 1:
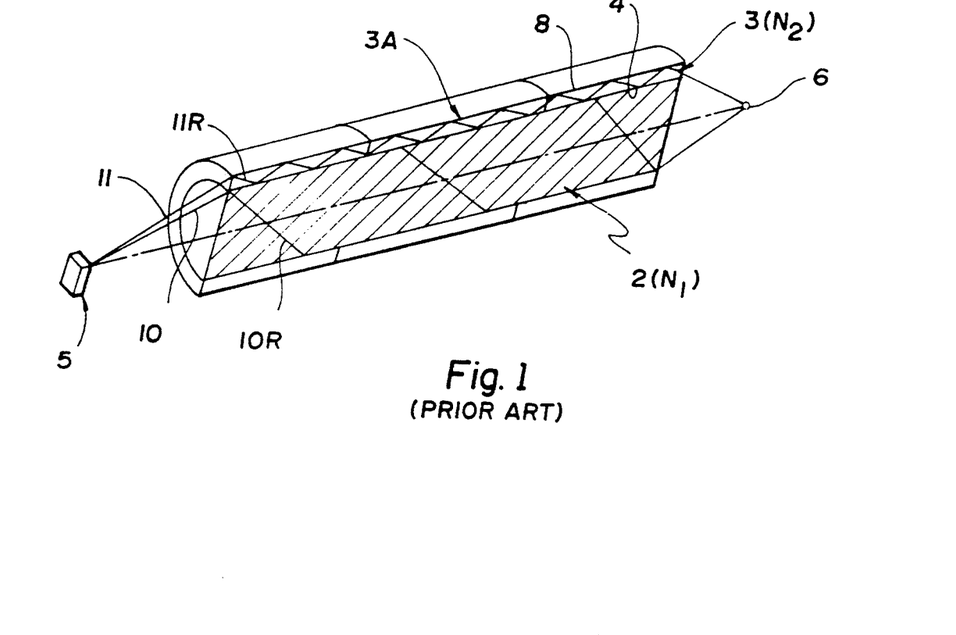
FIG. 1 is a perspective cut-away view of a known fiber optic system in which light is input by a light source to both the fiber optic core and the clad of a fiber optic element.

With reference to FIG. 1, there is shown a typical fiber optic sensor of the type having an analyte-responsive clad. The sensor 1 has a fiber optic core 2 constructed of a short length of glass fiber, such as silica fiber, having a diameter of approximately 1 mm or less and a length of approximately 50 mm or less. Surrounding the core is a clad 3 including a portion 3A made of a sensing material which is responsive to a chemical or analyte of interest, the clad 3, 3A typically having a depth of approximately 20 microns or less. The core 2 has a refractive index which is greater than the refractive index of the clad 3. As such, when light is input to the fiber optic core 2 from a light source or LED 5, light which is incident on the core-clad boundary interface 4 at a critical angle or greater (described below) will be totally internally reflected and transmitted along the core 2. However, when the sensor is in the presence of a chemical or analyte to which the clad portion 3A is particularly adapted to be responsive, the refractive index of clad portion 3A changes so that the amount and angles of light internally reflected from the core-clad interface 4 also changes. The resulting change in light transmission along core 2 in turn results in a change in the intensity and/or angle of light signals detected by photodetector 6, which change may be correlated to a known relationship between the chemical or analyte of interest and the clad.

The present inventors, in conducting numerous experiments with fiber optic sensors having analyte-sensitive clads, encountered stability and reliability problems which have generally plagued others in the field. The inventors' repeated testing of fiber optic sensors yielded unsatisfactory and inconsistent data due to the instability of light transmission along the fiber optic core. The causes of these problems have eluded those skilled in the art since the advent of this type of sensor. Although many attempts have been made to solve the problem through the use of various electronic arrangements and the like, the attempts have proven unsuccessful.

The present invention eliminates the stability and reliability problems associated with unstable light transmission along the core of a fiber optic sensor. To effectively stabilize core light transmission, the invention provides a method and apparatus for eliminating or controlling the independent propagation of light in the clad surrounding the core ("clad light"). As shown in FIG. 1, the input of light to the fiber optic sensor in known designs has been indiscriminate, with light from LED 5 being input to both the fiber optic core and the clad 3. The light input to the clad propagates along the clad, and is very sensitive to a host of factors. The inventors discovered that, apparently due in part to the short length of the fiber optic element in a fiber optic sensor, this independent clad light has a highly destabilizing effect on the transmission of light through the fiber optic core. The effect of this clad light has been to introduce sufficient "noise" as to substantially interfere with the light transmitted through the fiber optic core.

The destabilizing effect of clad light in fiber optic systems, as discovered by the present inventors, may be understood with reference to FIG. 1. The phenomenon of total internal reflection, upon which the fiber optic sensor relies for its basic functioning, is indicated by the ray of light 10 input to the fiber optic core 2 by the LED 5. Total internal reflection occurs by virtue of the relatively low refractive index $N_2$ of the clad in comparison with the relatively high refractive index $N_1$ of the core. Light rays input to core 2 which are incident on the interface 4 between the core 2 and the clad 3 at a critical angle or greater will be totally reflected. The critical angle, measured from the normal to the surface at which light enters the clad, is:

$$A_c = \sin^{-1} N_2/N_1$$

In FIG. 1, ray 10 from LED 5 is incident on the interface 4 at an angle which is greater than the critical angle $A_c$, so that ray 10 is totally internally reflected within the core.

In FIG. 1, the destabilizing effect of clad light in the fiber optic chemical sensor is indicated by the ray of light 11 input to the clad 3 by the LED 5. As shown in FIG. 1, light from LED 5 has heretofore been indiscriminately input to both the core and the clad of the fiber optic element, without any appreciation of the problems generated thereby. Because light is input to the clad, the phenomenon of total internal reflection, upon which the fiber optic sensor relies for its basic functioning in the transmission of light through the fiber optic core, also tends to occur in the clad. This total internal reflection effect within the clad occurs whenever the ambient medium surrounding clad 3 has a lower refractive index than that of the clad, i.e., lower than $N_2$. The phenomenon of total internal reflection of light ray 11 input to clad 3 occurs at the interface 8 between the clad and the ambient in essentially the same way as described above with respect to the interface 4 between the core 2 and the clad 3. Although the critical angle in clad 3 differs from the critical angle $A_c$ described above, and varies along clad portion 3A when the refractive index thereof changes in the presence of an analyte, light rays incident on interface 8 between the clad 3 and a surrounding medium having a lower refractive index than $N_2$, at an angle equal to greater than the relevant critical angle, will be totally reflected. Thus, ray 11 incident on interface 8 at an angle greater than the critical angle is totally internally reflected within the clad such that light independently propagates along the clad.

Even if the medium surrounding the clad 3 has a higher refractive index than the refractive index $N_2$ of the clad, so that the phenomenon of total internal reflection does not occur, some amount of light input to the clad will be reflected back into the clad at both interfaces 4 and 8, and propagated along the clad. Further, although the core 2 has a higher refractive index $N_1$ than the refractive index $N_2$ of the clad, so that no total internal reflection occurs at interface 4 with respect to the independently-propagated clad light, some amount of this clad light is reflected back into the clad at interface 4, while some amount of light is refracted through core 2. It will thus be understood that the light independently propagated along the clad is not limited to the simplistic zigzag pattern which is shown in FIG. 1 for ease of illustration, but rather will also in part be refracted into core 2 at interface 4.

The present inventors discovered that the foregoing clad light phenomenon, i.e., the reflection and refraction of light rays input to the clad 3 by photodetector 5 and propagated along the clad, produces sufficient "noise" as to interfere with the transmission of light through the fiber optic core and destabilize same. The deleterious effect of clad light on the stability and reliability of fiber optic systems which may be sensitive thereto, such as the effect of same on fiber optic sensors, has heretofore eluded those skilled in the art. As a consequence, for example, fiber optic sensors of the type having an analyte-reactive clad have heretofore proven so unstable and unreliable as to be incapable of functioning effectively to detect and/or measure analytes in a medium of interest.

The present invention eliminates the above-described destabilizing effect of clad light on the transmission of light through, and/or emission of light from, the fiber optic core by employing a field stop and/or clad light stop means suitably arranged relative to the core, the clad, and the LED or photodetector, of a fiber optic system. The invention thus vastly improves the reliability of the system, particularly where it takes the form of a fiber optic sensor, by stabilizing emitted signals and temperature conditions, and enhancing the sensor's resistance to stress.

In addition to eliminating the destabilizing effect of clad light, the invention further optimizes the transmission of light through the fiber optic core of a fiber optic system by providing an aperture stop means between the LED and the fiber optic core. Heretofore, fiber optic cores such as those employed in fiber optic sensors have exhibited considerable variability with respect to initial output signals, i.e., signals detected by the photodetector. Prior to compensation or amplification, output signals vary considerably from one fiber optic element to the next. In a system where an optimal initial output signal is approximately one volt, for example, various compensating and/or amplifying steps may be required in order to obtain the desired initial output signal from a given fiber optic element. To eliminate these problems, the present invention provides an aperture stop means between the LED and the fiber optic element, so as to focus the conical radiation pattern from the LED onto the fiber optic core. By varying the aperture size of the aperture stop means, the variability in initial output signals from one fiber optic element to the next can be effectively compensated for and eliminated.

SUMMARY OF THE INVENTION

The invention provides a fiber optic system comprising a light-transmissive fiber optic core substantially surrounded by a clad to define a fiber optic element, the clad being made of a material having a lower index of refraction than the index of refraction of the core; a light source operatively disposed relative to a light-receiving portion of the fiber optic element so as to input light thereto; detecting means, operatively arranged relative to the fiber optic element, for detecting changes in the transmission of light from the light source through the fiber optic element; and means for controlling light in the clad, whereby light from the fiber optic core which is incident on the detecting means is substantially unaffected by independent light propagation in the clad.

The invention also provides an improved fiber optic sensor including means for controlling the input of light to the fiber optic element of the sensor, such that light from the light source is substantially directed to a light-receiving end of the fiber optic core while light from the light source is substantially shielded from the clad.

Also provided in accordance with the invention is a method for controlling the propagation of light in the clad of a fiber optic sensor, whereby changes in light transmission through the fiber optic element, as detected by the detecting means, are substantially unaffected by independent light propagation in the clad. The method may also include the step of focusing light from the light source to the fiber optic core by arranging an aperture stop member between the light source and the light-receiving end of the fiber optic element. The focusing step may include the step of adjusting the size of the aperture of the aperture stop member so as to compensate for variations in different fiber optic elements.

The above and further objects, details and advantages of the invention will become apparent from the following detailed description, when read in conjunction with the accompanying drawings.

DETAILED DESCRIPTION OF PREFERRED EMBODIMENTS

Figure 2A:
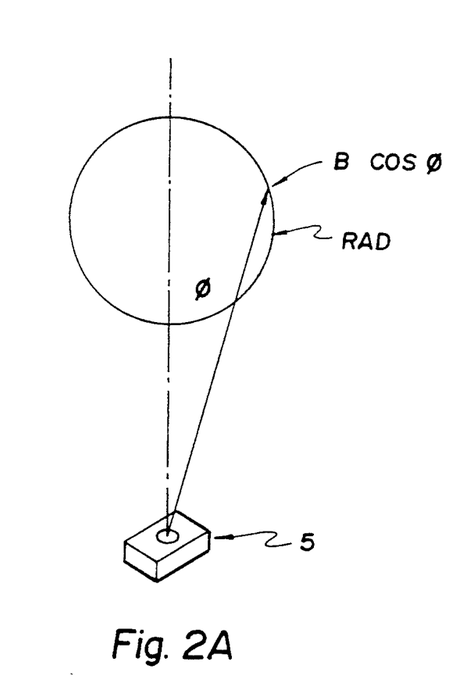
FIGS. 2A and 2B respectively depict the radiation pattern from an LED light source, and the focused radiation pattern from the LED in accordance with the aperture stop feature of the invention.
Figure 2B:
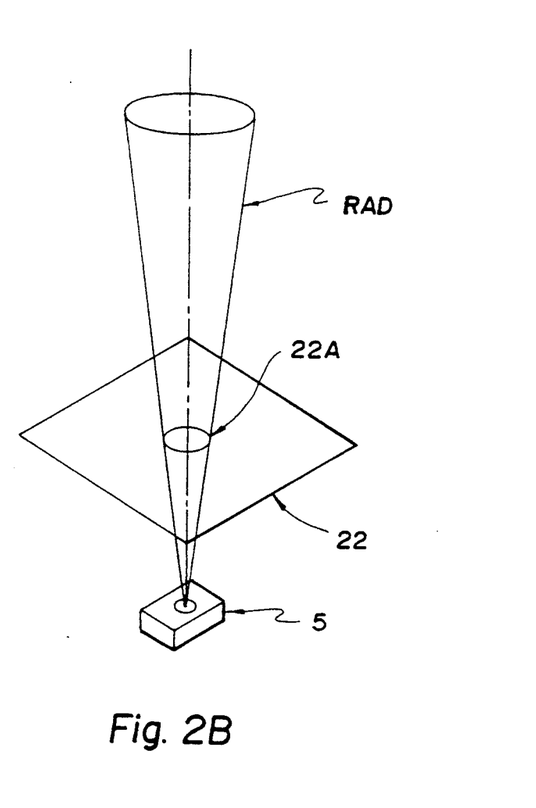
Figure 3:
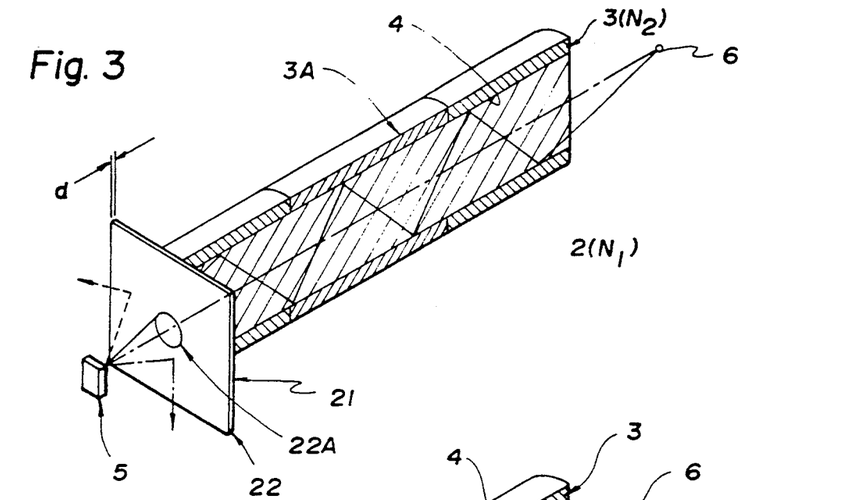
FIG. 3 illustrates a first preferred embodiment of the invention employing an aperture stop and field stop for focusing light to the core and eliminating the input of light to the clad, respectively.

With reference to FIGS. 2A, 2B and 3, a first preferred embodiment of the improved fiber optic system according to the invention will be described. In FIG. 3, a fiber optic element includes a fiber optic core 2 and surrounding clad 3, with a portion 3A of clad 3 being made of a material which is responsive to an analyte of interest. The refractive index $N_1$ of the core 2 is higher than the refractive index $N_2$ of clad 3. An LED 5 is coupled to a light receiving end of the fiber optic element, such as by a suitable socket member or the like (not shown). Arranged at the light-emitting end of the fiber optic element is a photodetector 6, which converts modulated light from the core into an electrical output signal which may be amplified for recording data.

Light input to core 2 by LED 5 is transmitted along the length of core 2 due to the phenomenon of total internal reflection, as described above with reference to FIG. 1. When the sensor is in the presence of a chemical or other analyte to which clad portion 3A is adapted to be responsive, the refractive index of clad portion 3A changes so that the amount and angles of light internally reflected from the core-clad interface 4 also changes. The change in light transmission along core 2 in turn results in a change in the intensity and/or angle of light signals detected by photodetector 6, which change may be correlated to a known relationship between the analyte of interest and the clad.

To eliminate the destabilizing effect of clad light in accordance with the present invention, a light-obstructing means in the form of a field stop 21 is disposed between the LED 5 and the fiber optic element. In the embodiment of FIG. 3, the field stop 21 is arranged adjacent to and behind an aperture stop member 22 such that the structure of field stop 21 is out of view. However, it will be understood that field stop 21 in FIG. 3 has essentially the same structure as field stop 21 shown in FIG. 4, i.e., field stop 21 comprises a flat member formed of a light-obstructing material and having a large central aperture 21A with a diameter which is substantially equal to or less than the diameter of the fiber optic core 2, while peripheral portions of field stop 21 entirely shield the light-receiving end of clad 3 from light. The field stop 21 is not limited to a rectangular shape as shown, and may instead be circular or any other desired shape. It will also be understood that the field stop 21 and the aperture stop 22 can be integrally combined as a single member as described below.

The provision of field stop 21 between the LED 5 and the fiber optic element prevents the input of light from LED 5 to the clad 3, while allowing light to pass through aperture 21A to the fiber optic core 2. As such, the clad light normally propagated along clad 3 (FIG. 1) is eliminated (FIG. 3). The transmission of light through core 2, as well as the output signals from photodetector 6, are thereby stabilized.

The aperture stop 22 in accordance with the invention, as shown in FIG. 3, comprises a flat member made of a light-obstructing material and having a central aperture 22A. The aperture stop 22 is positioned between LED 5 and field stop 21, however, aperture stop 22 can be used independently of field stop 21 by positioning same between LED 5 and the light-receiving end of the fiber optic element. It will also be understood that aperture stop 22 and field stop 21 can be formed integrally as a single member. Like the field stop 21, aperture stop 22 is not limited to the illustrative rectangular shape shown.

The effect of providing field stop 21 and aperture stop 22 between the LED and the fiber optic element to control input of light to the fiber optic element can best be understood with reference to FIGS. 2A and 2B. In FIG. 2A, the normal conically-shaped radiation pattern (RAD) of an LED is shown. Because light is emitted over a wide angular range, the resulting halo effect will normally result in light being input to the clad 3. Further, the bundle of light rays input to core 2 extends over a wide and unfocused angular range.

The provision of field stop 21 prevents light from the LED 5 from being input to the clad 3, thus eliminating the noise from clad light across the core-clad interface 4, which normally interferes with the transmission of light through the fiber optic core. By eliminating clad light, the field stop 21 vastly improves the reliability of the fiber optic sensor by stabilizing emitted signals and temperature conditions, and enhancing the sensor's resistance to stress.

The provision of aperture stop 22, which as discussed above may form an integral member with field stop 21, permits control of the size of the bundle of light rays input to core 2 (FIG. 2B). It will be understood that the size of aperture 22a of aperture stop 22 controls the light input to core 2, the diameter of aperture 22a being less than that of core 2. The size of aperture 22a may be varied to compensate for a number of variables. For example, the diameter of aperture 22a may be made smaller where aperture stop 22 is disposed a distance from the end of the fiber optic element, and larger where aperture stop 22 is disposed relatively close to or adjacent the end of the fiber optic element. Moreover, the size of aperture 22a may be varied to compensate for variations in the fiber optic element. The initial output signals from one fiber optic element to the next very considerably due to numerous factors, a problem which has heretofore required various compensation and/or amplification steps in order to produce an optimal initial output signal such as, for example, approximately one volt. By merely varying the size of aperture 22a of aperture stop 22, the present invention provides a simple and convenient means for consistently producing optimal initial output signals from one fiber optic element to the next.

The aperture stop feature of the invention provides a number of other advantages. Although heretofore it has been necessary to specially treat the light-receiving end of the fiber optic element to ensure that the end of the core is very smooth, the aperture stop of the invention essentially eliminates any need to smoothen the end of the core. Even if the light-receiving end of the core is left in a relatively rough condition, the control of light input from the LED by means of aperture stop 22, and/or the elimination of clad light by field stop 21, ensures consistent and reliable functioning of the fiber optic element. The aperture stop feature also affords very efficient use of an LED, minimizing required current so as to avoid burn-out of the LED, and even permitting the use of less expensive low power LEDs.

Figures 4, 5:
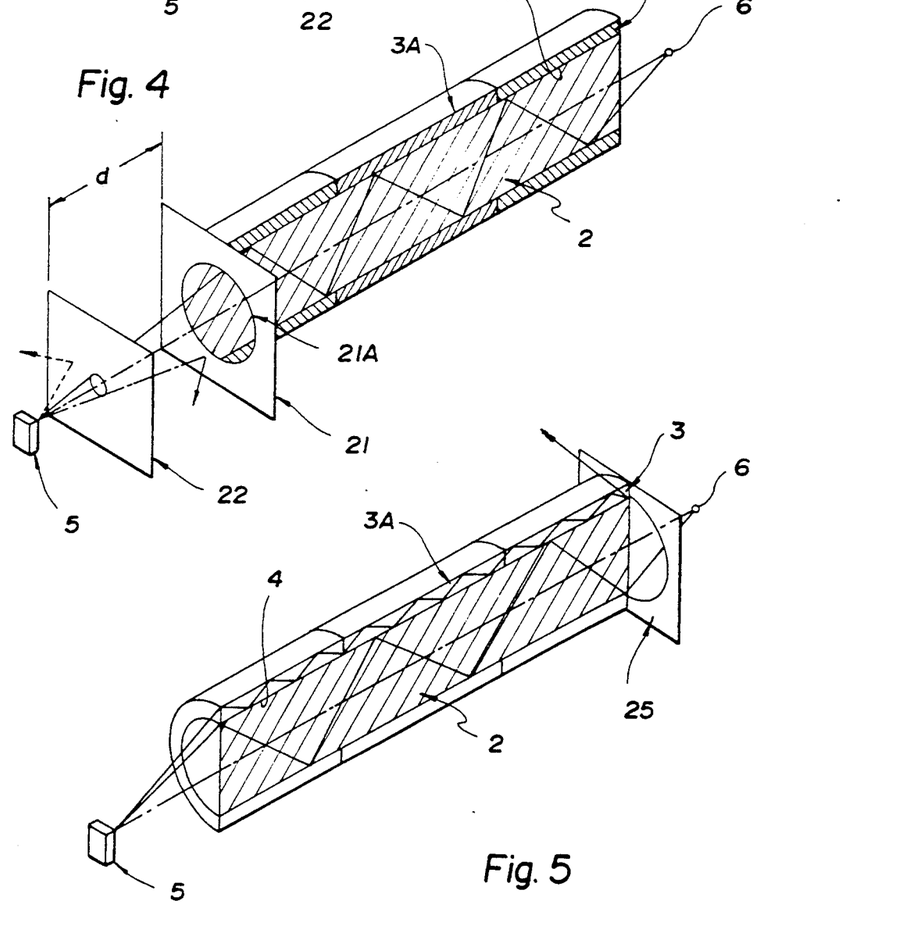
FIG. 4 shows a second embodiment in which the aperture stop and field stop of the invention are separated.
FIG. 5 depicts a third embodiment of the invention which employs a clad light stop diaphragm at the light-emitting end of the fiber optic element to prevent clad light from reaching the photodetector.

The FIG. 3 arrangement of field stop 21 and aperture stop 22 as adjacent or integral members is replaced in FIG. 4 by a separated arrangement of field stop 21 and aperture stop 22, with aperture stop 22 being relatively closer to LED 5 than field stop 21. In this embodiment, the diameter of aperture 22A of aperture stop 22 is relatively smaller than in FIG. 1. It will be understood in this respect that the relative distances between the LED 5, aperture stop 22 and field stop 21, as well as the diameter of aperture 22A, can be varied as necessary to obtain optimal light transmission through core 2.

In the FIG. 5 embodiment of the invention, the field stop 21 is replaced by a clad light stop diaphragm 25 at the light-emitting end of the fiber optic element. The structure of diaphragm 25 is similar to that of field stop 21, i.e., it comprises a substantially flat member with a central aperture having a diameter which is substantially equal to or less than the diameter of core 2. Although the overall shape of diaphragm 25 is shown as rectangular, diaphragm 25 can alternatively be formed in any other desired shape, provided it serves to effectively shield the light-emitting end of clad 3.

By positioning diaphragm 25 between the light-emitting end of the fiber optic element and the photodetector 6, clad light which has propagated along clad 3 is completely obstructed from photodetector 6 such that no clad light is incident on photodetector 6. Unlike the embodiment of FIGS. 3 and 4, in which field stop 21 prevents the occurrence of the clad light phenomenon, the embodiment of FIG. 5 permits the clad light phenomenon to occur but blocks the clad light from photodetector 6. This embodiment may be desirable for fiber optic systems in which the clad light phenomenon may have advantageous effects on the overall functioning of the fiber optic system, while the deleterious interference effect of clad light otherwise incident upon photodetector 6 is prevented by diaphragm 25.

It will also be understood that it may be desirable to employ diaphragm 25 at the light-emitting end of the fiber optic element in conjunction with field stop 21 at the light-receiving end. The diaphragm 25 may also be employed in conjunction with the various other embodiments of the invention described below.

Figure 6:
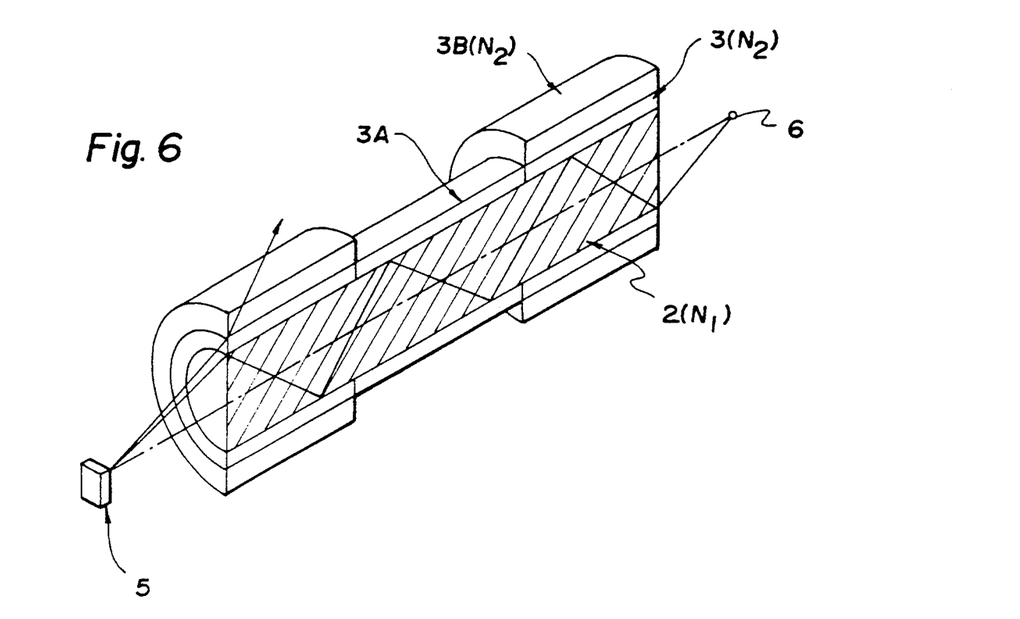
FIG. 6 illustrates a fourth embodiment of the invention in which supplemental clad portions having the same index of refraction as that of the main clad are employed to mitigate the effects of clad light.

In the embodiment of the invention shown in FIG. 6, the means for eliminating or mitigating the destabilizing effect of clad light on core light transmission takes the form of supplemental clad portions 3B provided so as to surround the clad 3 in all but the area of analyte-responsive portion 3A. Supplemental clad portions 3B are made of a material having a refractive index $N_2$ matched to that of the clad 3, and may be made of the same material as clad 3. The supplemental clad portions 3B mitigate the total internal reflection phenomenon otherwise occurring at the clad-ambient interface, thus mitigating or eliminating the destabilizing effect of clad light on the transmission of light through the core.

Figure 7:
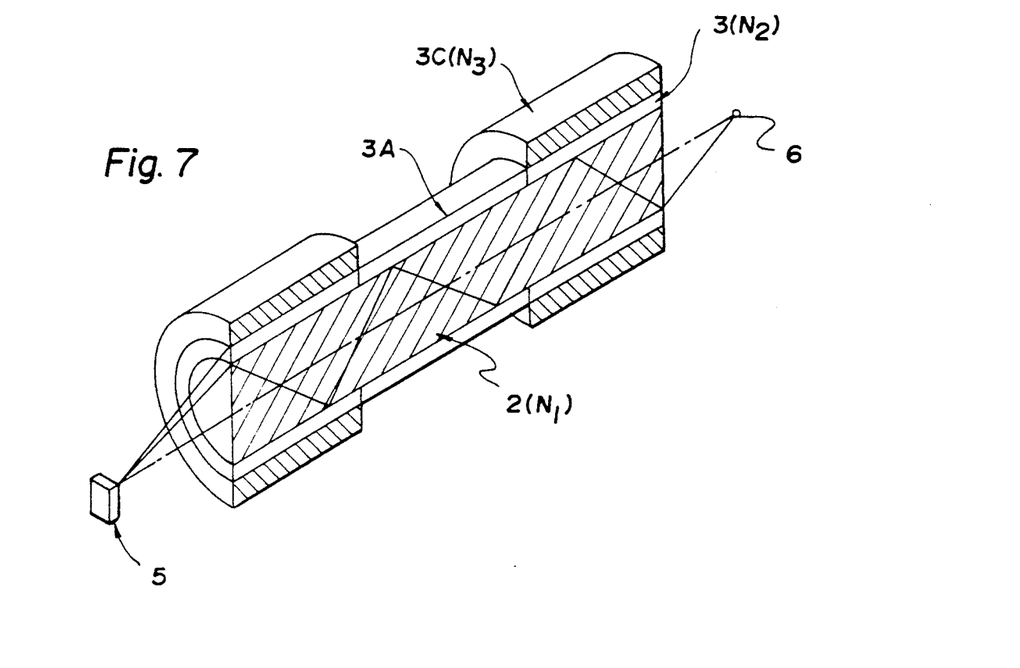
FIG. 7 depicts a fifth embodiment of the invention in which supplemental clad portions having a higher index of refraction than that of the main clad are employed to mitigate or substantially eliminate clad light.

The embodiment of the invention shown in FIG. 7 is similar to that of FIG. 6, except that here the supplemental clad portions 3C are formed of a material having a higher index of refraction $N_3$ than that of the clad 3 ($N_2$). In this embodiment, the supplemental clad portions 3C essentially eliminate the total internal reflection phenomenon otherwise occurring at the interface between the clad and the ambient by effectively absorbing clad light.

Figures 8, 9, 10:
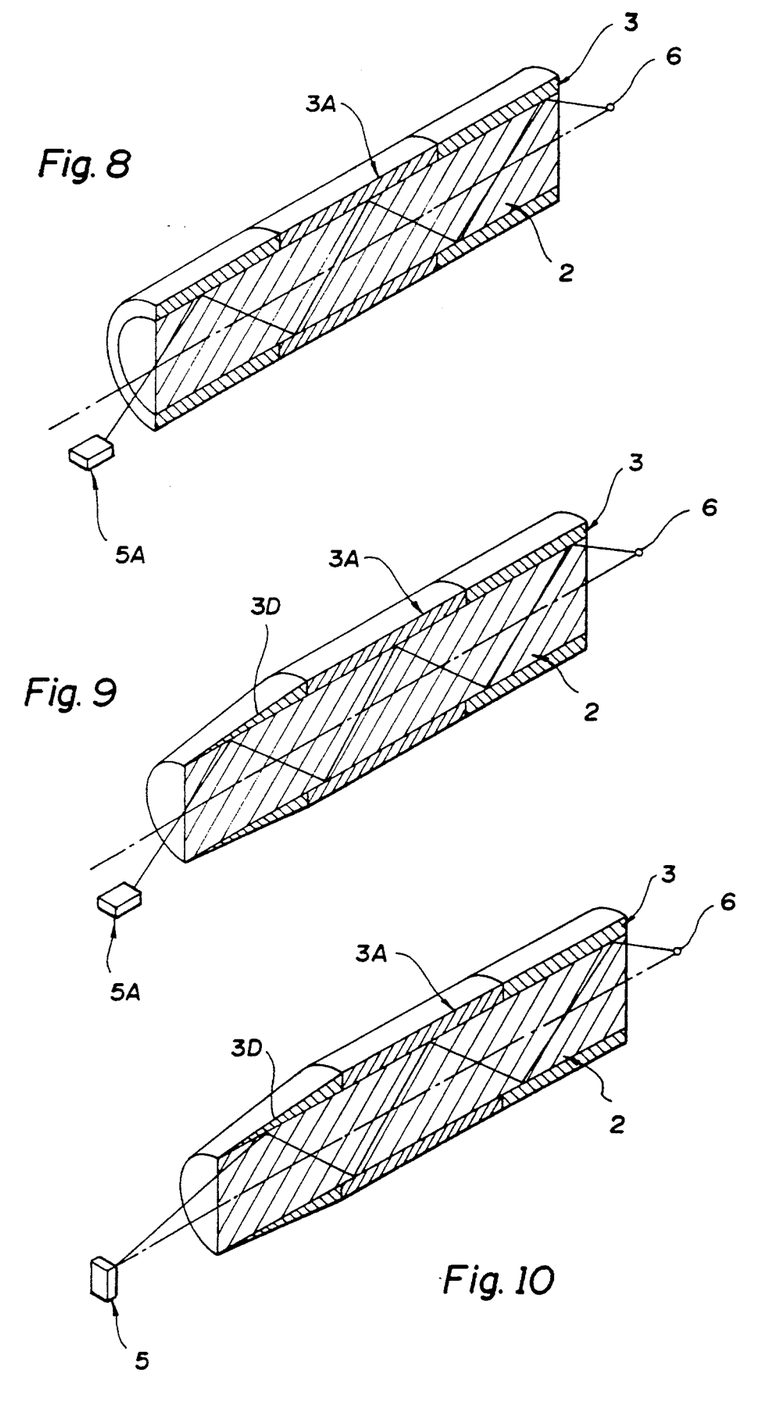
FIG. 8 shows a sixth embodiment of the invention employing an edge-type LED light source to mitigate clad light.
FIG. 9 depicts a seventh embodiment of the invention in which a tapered-end clad portion is combined with an edge-type LED light source to mitigate or substantially eliminate clad light.
FIG. 10 shows an eighth embodiment of the invention in which a tapered-end clad portion is employed with a surface-type LED light source to mitigate clad light.

In FIG. 8, the LED 5 of the surface-source type as employed in the foregoing embodiments is replaced by an LED 5A of an edge-source type, in which light is emitted from an edge portion of the LED. In this embodiment, the input of light to the clad is mitigated or substantially eliminated by virtue of the more focused input of light to core 2 by the edge-source LED 5A.

FIG. 9 depicts an arrangement employing the edge-source type LED 5A of FIG. 8 in combination with a tapered clad portion 3D at the light-receiving end of the fiber optic element. The tapered clad portion 3D is gradually tapered from the analyte-responsive portion 3A such that the clad material is essentially absent at the light-receiving end of the fiber optic element. There thus remains essentially no clad material to which the focused light from the edge-source LED 5A can be input, thus eliminating the phenomenon of clad light.

FIG. 10 depicts an embodiment employing the tapered clad portion 3D of FIG. 9, and substituting a surface-source type LED 5 for the edge-source type employed in FIG. 9. In FIG. 10, even though light from the surface-source type LED 5 is relatively less focused than that from an edge-source type LED, the elimination of clad material from the light-receiving end of the fiber optic element ensures that no light will be input to the clad.

It will be understood from the foregoing that a principal feature of the present invention is to eliminate and/or control the destabilizing effect of clad light, independently input to and propagated along the clad, on the transmission of light through the fiber optic core in a fiber optic system. While the various embodiments of the invention have been described with respect to a fiber optic sensor of the type having a clad which is responsive to an analyte, it will be understood that the invention is applicable to essentially any fiber optic system in which clad light has a destabilizing effect on core light transmission.

The invention is not limited to the particular embodiments described above for mitigating or eliminating clad light, and various other means may be employed. For example, the field stop means at the light-receiving end of the fiber optic element may take the form of a light-obstructing coating material applied directly to the end of the clad to cover same. Likewise, the clad light stop diaphragm 25 of FIG. 5 may be replaced by a coating of light-obstructing material applied directly to the light-emitting end of the clad. Similarly, the tapered clad portion 3D described with reference to FIGS. 9 and 10 may also be provided at the light-emitting end of the fiber optic element.

The second principal feature of the invention is the aperture stop means provided at the light-receiving end of the fiber optic element. As described above, the aperture stop means and the field stop means according to the invention may take the form of a single unitary member interposed between the LED and the light-receiving end of the fiber optic element to simultaneously focus light on the core 2 while shielding the clad 3 from any light input. It is also contemplated that the aperture stop means may be employed independently of the field stop means by arranging the aperture stop some distance from the light-receiving end of the fiber optic element. In such an arrangement, the diaphragm 25 may for example be employed at the light-emitting end of the element to prevent clad light from reaching the photodetector.

While there have been described what are at present considered to be the preferred embodiments of the invention, it will be understood that various modifications may be made therein without departing from the spirit and scope of the invention. The present embodiments are therefore to be considered in all respects as illustrative, and not restrictive. The scope of the invention is indicated by the appended claims rather than by the foregoing description.

We claim:

1. A fiber optic system, comprising:
   a light-transmissive fiber optic core substantially surrounded by a clad, said core and clad together defining a fiber optic element;
   said clad being made of a material having a lower index of refraction than the index of refraction of said core;
   a light source disposed adjacent a light-receiving portion of said fiber optic element so as to input light thereto;
   detecting means, disposed adjacent said fiber optic element, for detecting changes in the transmission of light from said light source through said fiber optic element;
   means for controlling light in said clad, whereby light from said fiber optic core which is incident on said detecting means is substantially unaffected by independent light propagation in said clad; and
   said light controlling means comprising a field stop disposed between said light source and said light-receiving portion of said fiber optic element, said field stop having a central opening which permits light from said light source to pass therethrough to said fiber optic core, while peripheral portions of said field stop shield said clad to prevent the input of light thereto from said light source.

2. A fiber optic system, comprising:
   a light-transmissive fiber optic core substantially surrounded by a clad, said core and clad together defining a fiber optic element;
   said clad being made of a material having a lower index of refraction than the index of refraction of said core;
   a light source disposed adjacent a light-receiving portion of said fiber optic element so as to input light thereto;
   detecting means, disposed adjacent said fiber optic element, for detecting changes in the transmission of light from said light source through said fiber optic element;
   means for controlling light in said clad, whereby light from said fiber optic core which is incident on said detecting means is substantially unaffected by independent light propagation in said clad;
   said light-controlling means comprising field stop means, disposed at said light-receiving portion of said fiber optic element, for obstructing light from said light source to said clad;
   said light source comprising an LED; and
   said system further comprising aperture stop means, disposed between said LED and said light-receiving portion of said fiber optic element, so as to control the input of light from said LED to said fiber optic core.

3. A fiber optic system according to claim 2, wherein: said field stop means and said aperture stop means are formed as a unitary element.

4. A fiber optic sensor according to claim 2, wherein: said aperture stop means is provided with a central aperture having a diameter which is substantially less than the diameter of said fiber optic core.

5. A fiber optic system according to claim 1, further comprising:
   a clad light stop diaphragm disposed between a light-emitting portion of said fiber optic element and said detecting means.

6. A fiber optic system, comprising:
   a light-transmissive fiber optic core substantially surrounded by a clad, said core and clad together defining a fiber optic element;
   said clad being made of a material having a lower index of refraction than the index of refraction of said core;
   a light source disposed adjacent a light-receiving portion of said fiber optic element so as to input light thereto;
   detecting means, disposed adjacent said fiber optic element, for detecting changes in the transmission of light from said light source through said fiber optic element;
   means for controlling light in said clad, whereby light from said fiber optic core which is incident on said detecting means is substantially unaffected by independent light propagation in said clad;
   said light-controlling means comprising field stop means, disposed at said light-receiving portion of said fiber optic element, for obstructing light from said light source to said clad;
   said field stop means comprising a substantially flat light-obstructing member having a central opening which permits light to pass therethrough to said fiber optic core;

said central opening having a diameter substantially equal to or less than the diameter of said fiber optic core; and said light-obstructing member including a light shield portion of sufficient area to entirely shield said clad from light from said light source.

7. A fiber optic system, comprising:

a light-transmissive fiber optic core substantially surrounded by a clad, said core and clad together defining a fiber optic element;

said clad being made of a material having a lower index of refraction than the index of refraction of said core;

a light source disposed adjacent a light-receiving portion of said fiber optic element so as to input light thereto;

detecting means, disposed adjacent said fiber optic element, for detecting changes in the transmission of light from said light source through said fiber optic element;

means for controlling light in said clad, whereby light from said fiber optic core which is incident on said detecting means is substantially unaffected by independent light propagation in said clad;

said light-controlling means comprising field stop means, disposed at said light-receiving portion of said fiber optic element, for obstructing light from said light source to said clad; and said field stop means comprising a supplemental clad portion surrounding said clad along at least the light-receiving portion of said fiber optic element.

8. A fiber optic system, comprising:

a light-transmissive fiber optic core substantially surrounded by a clad, said core and clad together defining a fiber optic element;

said clad being made of a material having a lower index of refraction than the index of refraction of said core;

a light source disposed adjacent a light-receiving portion of said fiber optic element so as to input light thereto;

detecting means, disposed adjacent said fiber optic element, for detecting changes in the transmission of light from said light source through said fiber optic element;

means for controlling light in said clad, whereby light from said fiber optic core which is incident on said detecting means is substantially unaffected by independent light propagation in said clad;

said light-controlling means comprising field stop means, disposed at said light-receiving portion of said fiber optic element, for obstructing light from said light source to said clad; and said field stop means comprising a tapered clad portion provided at the light-receiving portion of said fiber optic element.

9. A fiber optic system according to claim 8, wherein:

said light-controlling means further comprises an edge-source type LED defining said light source, the light from said LED being focused substantially on said fiber optic core.

10. In a fiber optic sensor for sensing an analyte of interest, said sensor including a fiber optic element defined by a light-transmissive fiber optic core substantially surrounded by a clad, the clad being made of a material having a lower index of refraction than that of the core, at least a portion of the clad being reactive with a predetermined analyte to produce changes in light transmission through the core in the presence of the predetermined analyte, a light source disposed adjacent a light-receiving end of the fiber optic element so as to input light thereto, and detecting means disposed adjacent the fiber optic element for detecting changes in light transmission from the light source through the fiber optic element, the improvement comprising:

means for controlling the input of light to said fiber optic element such that light from said light source is substantially directed to a light-receiving end of said fiber optic core while light from said light source is substantially shielded from said clad; and said light controlling means comprising a field stop disposed between said light source and said light-receiving portion of said fiber optic element, said field stop having a central opening which permits light from said light source to pass therethrough to said fiber optic core, while peripheral portions of said field stop shield said clad to prevent the input of light thereto from said light source.

11. In a fiber optic sensor for sensing an analyte of interest, said sensor including a fiber optic element defined by a light-transmissive fiber optic core substantially surrounded by a clad, the clad being made of a material having a lower index of refraction than that of the core, at least a portion of the clad being reactive with a predetermined analyte to produce changes in light transmission through the core in the presence of the predetermined analyte, a light source disposed adjacent a light-receiving end of the fiber optic element so as to input light thereto, and detecting means disposed adjacent the fiber optic element for detecting changes in light transmission from the light source through the fiber optic element, the improvement comprising:

means for controlling the input of light to said fiber optic element such that light from said light source is substantially directed to a light-receiving end of said fiber optic core while light from said light source is substantially shielded from said clad;

said light-controlling means comprising field stop means, disposed between said light source and said light-receiving end of said fiber optic element, for obstructing light from said light source to said clad;

said light source comprising an LED; and said light-controlling means further comprising aperture stop means for focusing light from said light source onto the light-receiving end of said fiber optic element.

12. An improved fiber optic sensor according to claim 11, wherein:

said field stop means and said aperture stop means are formed as a unitary element.

13. An improved fiber optic sensor according to claim 11, wherein:

said field stop means is disposed adjacent said light-receiving end of said fiber optic element; and said aperture stop means is disposed between said field stop means and said light source.

14. An improved fiber optic sensor according to claim 10, further comprising:

a clad light stop diaphragm disposed between said detecting means and a light-emitting end portion of said fiber optic element.

15. In a fiber optic sensor for sensing an analyte of interest, said sensor including a fiber optic element defined by a light-transmissive fiber optic core substantially surrounded by a clad, the clad being made of a material having a lower index of refraction than that of the core, at least a portion of the clad being reactive with a predetermined analyte to produce changes in light transmission through the core in the presence of the predetermined analyte, a light source disposed adjacent a light-receiving end of the fiber optic element so as to input light thereto, and detecting means disposed adjacent the fiber optic element for detecting changes in light transmission from the light source through the fiber optic element, the improvement comprising:

means for controlling the input of light to said fiber optic element such that light from said light source is substantially directed to a light-receiving end of said fiber optic core while light from said light source is substantially shielded from said clad;

said light-controlling means comprising field stop means, disposed between said light source and said light-receiving end of said fiber optic element, for obstructing light from said light source to said clad;

said field stop means comprising a substantially flat light-obstructing member having a central opening which permits light to pass therethrough to said fiber optic core;

said central opening having a diameter substantially equal to or less than the diameter of said fiber optic core; and said light-obstructing member including a light shield portion of sufficient area to entirely shield said clad from light from said light source.

16. In a fiber optic sensor for sensing an analyte of interest, said sensor including a fiber optic element defined by a light-transmissive fiber optic core substantially surrounded by a clad, the clad being made of a material having a lower index of refraction than that of the core, at least a portion of the clad being reactive with a predetermined analyte to produce changes in light transmission through the core in the presence of the predetermined analyte, a light source disposed adjacent a light-receiving end of the fiber optic element so as to input light thereto, and detecting means disposed adjacent the fiber optic element for detecting changes in light transmission from the light source through the fiber optic element, the improvement comprising:

means for controlling the input of light to said fiber optic element such that light from said light source is substantially directed to a light-receiving end of said fiber optic core while light from said light source is substantially shielded from said clad;

said light-controlling means comprising field stop means, disposed between said light source and said light-receiving end of said fiber optic element, for obstructing light from said light source to said clad; and said field stop means comprising a supplemental clad portion surrounding said clad along at least the light-receiving portion of said fiber optic element.

17. In a fiber optic system for sensing an analyte of interest, said sensor including a fiber optic element defined by a light-transmissive fiber optic core substantially surrounded by a clad, the clad being made of a material having a lower index of refraction than that of the core, at least a portion of the clad being reactive with a predetermined analyte to produce changes in light transmission through the core in the presence of the predetermined analyte, a light source disposed adjacent a light-receiving end of the fiber optic element so as to input light thereto, and detecting means disposed adjacent the fiber optic element for detecting changes in light transmission from the light source through the fiber optic element, the improvement comprising:

means for controlling the input of light to said fiber optic element such that light from said light source is substantially directed to a light-receiving end of said fiber optic core while light from said light source is substantially shielded from said clad;

said light-controlling means comprising field stop means, disposed between said light source and said light-receiving end of said fiber optic element, for obstructing light from said light source to said clad; and said field stop means comprising a tapered clad portion provided at the light-receiving portion of said fiber optic element.

18. An improved fiber optic system according to claim 17, wherein:

said light-controlling means further comprises an edge-source type LED defining said light source, the light from said LED being focused substantially on said fiber optic core.

19. A method of stabilizing the transmission of light through a fiber optic sensor, the sensor including a fiber optic element defined by a light-transmissive fiber optic core substantially surrounded by a clad, the clad being made of a material having a lower index of refraction than that of the core and being reactive with a predetermined analyte to produce changes in light transmission through the core in the presence of the predetermined analyte, a light source disposed adjacent the fiber optic element so as to input light thereto, and detecting means disposed adjacent the fiber optic element for detecting changes in light transmission from the light source through the fiber optic element, comprising the step of:

controlling the propagation of light in said clad, whereby changes in light transmission through said fiber optic element, as detected by said detecting means, are substantially unaffected by independent light propagation in said clad;

said clad light controlling step comprising arranging a field stop between said light source and a light-receiving end of said fiber optic element, said field stop having a central opening which permits light from said light source to pass therethrough to said fiber optic core, while peripheral portions of said field stop shield said clad to prevent the input of light thereto from said light source.

20. A method of stabilizing the transmission of light through a fiber optic sensor, the sensor including a fiber optic element defined by a light-transmissive fiber optic core substantially surrounded by a clad, the clad being made of a material having a lower index of refraction than that of the core and being reactive with a predetermined analyte to produce changes in light transmission through the core in the presence of the predetermined analyte, a light source disposed adjacent the fiber optic element so as to input light thereto, and detecting means disposed adjacent the fiber optic element for detecting changes in light transmission from the light source through the fiber optic element, comprising the step of:

controlling the propagation of light in said clad, whereby changes in light transmission through said fiber optic element, as detected by said detecting means, are substantially unaffected by independent light propagation in said clad;

said clad light controlling step comprising arranging a clad light stop diaphragm between said detecting means and a light-emitting end portion of said fiber optic element, said clad light stop diaphragm including a central aperture for permitting light from said fiber optic core to reach said detecting means.

21. A method of stabilizing the transmission of light through a fiber optic sensor, the sensor including a fiber optic element defined by a light-transmissive fiber optic core substantially surrounded by a clad, the clad being made of a material having a lower index of refraction than that of the core and being reactive with a predetermined analyte to produce changes in light transmission through the core in the presence of the predetermined analyte, a light source disposed adjacent the fiber optic element so as to input light thereto, and detecting means disposed adjacent the fiber optic element for detecting changes in light transmission from the light source through the fiber optic element, comprising the steps of:
controlling the propagation of light in said clad, whereby changes in light transmission through said fiber optic element, as detected by said detecting means, are substantially unaffected by independent light propagation in said clad; and
focusing light from said light source to said fiber optic core by arranging an aperture stop member between said light source and a light-receiving end of said fiber optic element.

22. The method of claim 21, wherein:
said focusing step comprises adjusting the size of an aperture of said aperture stop member to compensate for variations in different fiber optic elements.

* * * * *

UNITED STATES PATENT AND TRADEMARK OFFICE
CERTIFICATE OF CORRECTION

PATENT NO. : 5,274,721
DATED : December 28, 1993
INVENTOR(S) : Dickinson et al.

It is certified that error appears in the above-indentified patent and that said Letters Patent is hereby corrected as shown below:

Column 3, line 27, after "to" insert --or--.

Signed and Sealed this

Twenty-sixth Day of April, 1994

Attest:

BRUCE LEHMAN

Attesting Officer     Commissioner of Patents and Trademarks